United States Patent [19]

Regnier et al.

[11] Patent Number: 4,999,372

[45] Date of Patent: Mar. 12, 1991

[54] NEW AMINOCHROMANOL COMPOUNDS

[75] Inventors: Gilbert Regnier, Chatenay Malabry; Alain Dhainaut, Chatou; Jean-Paul Vilaine, Chatenay Malabry; Nicole Villeneuve, Rueil Malmaison; Ghislaine Joly, Neuilly s/Seine; Jacques Duhault, Croissy s/Seine, all of France

[73] Assignee: ADIR et Compagnie, Neuilly-sur-Seine, France

[21] Appl. No.: 419,824

[22] Filed: Oct. 11, 1989

[30] Foreign Application Priority Data

Oct. 17, 1988 [FR] France .................. 88 13637

[51] Int. Cl.[5] .................. C07D 405/04; A61K 31/35; A61K 31/40
[52] U.S. Cl. .................. 514/422; 514/423; 548/525
[58] Field of Search .................. 548/525; 514/422, 423

[56] References Cited

U.S. PATENT DOCUMENTS 4,048,317  9/1977  Watts .................. 548/525
4,631,282  12/1986  Cassidy .................. 548/525
4,831,050  5/1989  Cassidy et al. .................. 548/525

Primary Examiner—Cecilia Shen
Assistant Examiner—Celia Chang
Attorney, Agent, or Firm—Gordon W. Hueschen

[57] ABSTRACT

New aminochromanol compounds of the formula:

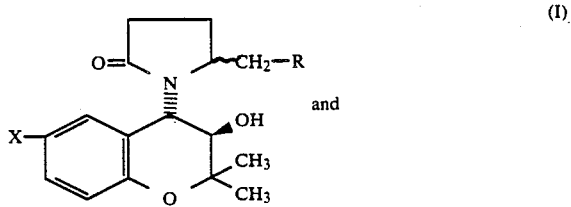

and

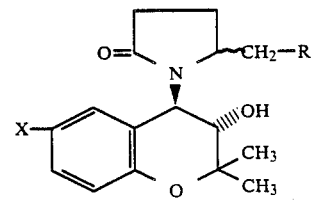

in which

X is cyano, nitro, trifluoromethyl, alkoxycarbonyl, carbamido, dialkylcarbamido, aminosulfonyl, dialkylaminosulfonyl, alkylsulfonyl, alkylsulfonylamino or acyl;

$CH_2$-R is attached (in the 5 position of the pyrrolidinone nucleus) to an R- or S-configured carbon atom, and R is:

either OR' or SR' in which R' is hydrogen, ($C_1$–$C_{10}$)-alkyl, ($C_1$–$C_5$-alkyl)-carbonyl or

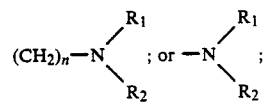

and physiologically tolerable acid addition salts thereof, in the case where R contains a basic function.

These compounds and their physiologically tolerable salts can be used in therapeutics for the activation of potassium channels, especially in the treatment of disorders associated with abnormal smooth muscle contraction and in the cardiovascular, bronchopulmonary, digestive, urinary and uterine fields.

8 Claims, No Drawings

NEW AMINOCHROMANOL COMPOUNDS

The present invention provides aminochromanol compounds of the general formula I:

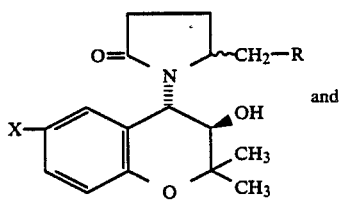

and

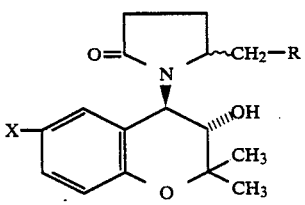

in which:

X is selected from the group consisting of: a cyano radical, a nitro radical, a trifluoromethyl radical, alkoxycarbonyl radicals in which the alkoxy groups contain from 1 to 5 carbon atoms, in straight and branched chains, a carbamido radical, dialkylcarbamido radicals, an aminosulfonyl radical, dialkylaminosulfonyl radicals, alkylsulfonyl radicals and alkylsulfonylamino radicals in which the alkyl groups each contain from 1 to 5 carbon atoms, and acyl radicals selected from: acetyl, propionyl, benzoyl and trifluoroacetyl radicals;

CH2-R is attached (in the 5 position of the pyrrolidinone nucleus) to an R- or S- configured carbon atom, and R is selected from the group consisting of:

(a) -OR' and SR' radicals in which R' is selected from the group consisting of:
 a hydrogen atom;
 alkyl and hydroxyalkyl radicals having up to 10 carbon atoms in straight and branched chains, and such chains interrupted by one or more oxygen atoms;
 alkylcarbonyl radicals in which the alkyl groups contain up to 5 carbon atoms in straight and branched chains;

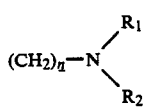

radicals in which:
n is an integer from 2 to 5, and $R_1$ and $R_2$, which are identical or different, are each selected from the group consisting of:
a hydrogen atom,
alkyl radicals having from 1 to 5 carbon atoms in straight and branched chains, and
$R_1$ and $R_2$ together with the nitrogen atom to which they are bonded, form rings having 4 and 5 carbon atoms, and these rings containing another hetero atom selected from oxygen and sulfur atoms and a-N-$R_3$ group in which $R_3$ is selected from the group consisting of:
a hydrogen atom,
alkyl radicals having from 1 to 5 carbon atoms in straight and branched chains, and
an -A-Z radical in which
A is selected from: a single bond, saturated $C_1$-$C_5$ hydrocarbon chains, and such chains containing a double bond, and
Z is selected from the group consisting of:
 a hydroxy radical,
 a benzhydryl radical,
 an unsubstituted phenyl radical,
 phenyl radicals mono and poly substituted by halogen atoms, trifluoromethyl, $C_1$-$C_5$ alkoxy and methylene dioxy radicals, and
 penta and hexagonal heterocyclic radicals containing one and more oxygen, nitrogen and sulfur atoms, selected from pyridyl, thiazolyl, pyrimidinyl and pyrazinyl radicals, and such radicals mono and poly-substituted by halogen atoms, alkyl and alkoxy radicals each having from 1 to 5 carbon atoms and,

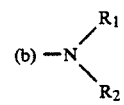

radicals in which $R_1$ and $R_2$ have the meanings given above.

The nearest prior art to the present invention is illustrated especially by:
J. M. EVANS et al., Med. Chem. 29 (II) 2194–2201 (1986); and
the European patent Application published under no. 0076705 on 06.04.1983 which relates to benzopyran compounds of which the leader product is CROMAKALIM corresponding to the formula:

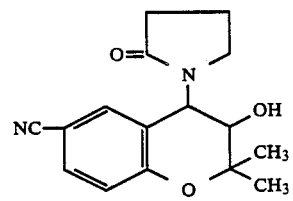

which formula does not contain a substituent on the pyrrolidone nucleus.

It has been found in investigation carried out by the applicants that the introduction of a substituent into the position α to the nitrogen atom of the pyrrolidone nucleus results in the compounds I of the present invention which are pure diastereoisomers which, compared with the racemic derivative, which is what CROMAKALIM is, have a particularly valuable advantage as regards therapeutic use.

The compounds of the present invention, whose pharmacological profile is that of potassium agonist which can be used especially in the cardiovascular field, have, depending on the particular compound, a physiological activity comparable or superior to that of CROMAKALIM, with a duration of action much longer than that of the latter, hence their great advantage in therapeutic use.

The present invention also relates to a process for the preparation of the compounds of the general formula I according to reaction scheme A:

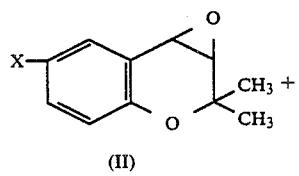

(II)

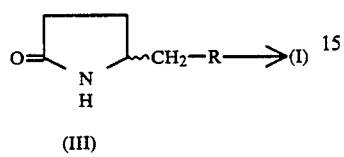

(III)

characterised in that an equimolar amount of the chroman compound of the general formula II, in which X has the meaning defined above, is reacted with the R- or S-configured chiral pyrrolidone compound of the general formula III, in which R has the meaning defined above, in the form of the sodium or lithium salt. It is especially advantageous to carry out the reaction in an aprotic solvent at a temperature of from 20° to 50° C.

Examples of especially suitable aprotic solvents are dimethyl sulphoxide, hexamethylphosphorotriamide, dimethylformamide and dimethylacetamide.

Pyrrolidone III must be converted beforehand into the sodium or lithium salt by means of sodium hydride or butyllithium, in the solvent chosen to carry out the reaction.

The chroman compounds II can be prepared according to the technique of J. M. EVANS et al., J. Med. Chem. 26 (II) 1582-1589 (1983) and E.P. No. 0076075.

The R- or S-configured chiral pyrrolidone compounds III were prepared starting from natural R- or S-configured pyroglutamic acids, respectively, according to scheme B which follows:

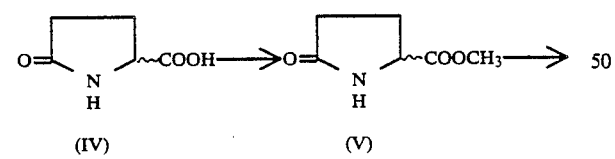

(IV)      (V)

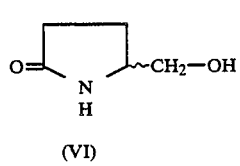

(VI)

described by S. SAIJO et al., Chem. Pharm. Bull. 28, 1449 (1980).

R- or S-pyroglutaminol VI can be used as starting material in the preparation of the chiral pyrrolidones III either directly, in the case where R=OR', according to scheme C:

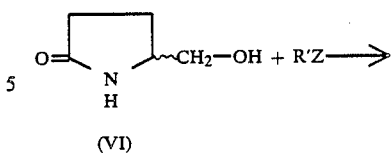

(VI)

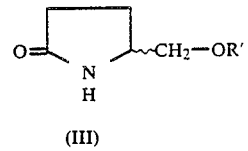

(III)

Z being a halogen atom, such as bromine or iodine, or a sulphate or arylsulphonate ion, and R' having the meaning defined above; the reaction generally being carried out in water or in an aprotic polar solvent in the presence of a strong base or a tertiary amine acting as acceptor of the acid formed;

or after conversion by known methods into a halogenated, preferably chlorinated, compound of the formula:

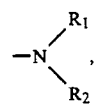

(VII)

which is reacted according to scheme D:

$$O{=}\underset{H}{\underset{N}{\bigsqcup}}{-}CH_2{-}Cl + HR \longrightarrow$$

(VII)

(VIII)

R representing either —OR' or SR' or $$-N\begin{matrix}R_1\\ \diagdown\\ R_2\end{matrix},$$

the reaction generally being effected according to known methods in an aprotic polar solvent, starting from an alkaline derivative of the compound R'OH or in the presence of an excess of amine $$HN\begin{matrix}R_1\\ \diagdown\\ R_2\end{matrix}$$

or of a tertiary base acting as acceptor of the hydracid formed.

In the particular case of the compounds of the formula I in which R represents OR' and R' represents a hydrogen atom, that is to say, in order to prepare the compounds of the formula I':

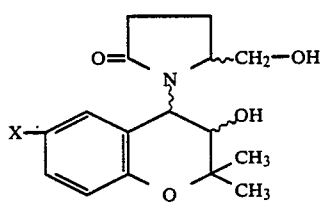

(I')

it is preferable to carry out the reaction in accordance with scheme A given above, starting from an R- or S-configured chiral pyrrolidone of the formula

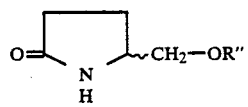

in which R" is a readily hydrolysable labile radical which can be prepared starting from compound VI and ethyl vinyl ether according to a technique described by S. SAIJO et al., Chem. Pharm. Bull. 28, 1449 (1980).

The compounds of the general formula I are diastereoisomeric chiral substances. The method of synthesis according to scheme A always provides aminochromanols I in the trans-configuration by opening the epoxide function, and the use of S- or R-configured pyrrolidone III will give (after separation by column chromatography or by formation of salts and crystallisation of the latter where R contains a basic function) two pairs of pure diastereoisomers having the configuration 3S,4R,5'S and 3R,4S,5'S or 3S,4R,5'R and 3R,4S,5'R.

Separation on a column is effected by flash chromatography, under nitrogen pressures of from 0.5 to 1 bar, with 35–70μ silica and solvent systems such as: $CH_2Cl_2$/methanol or $CH_2Cl_2$/ethyl acetate.

Salt formation can be effected starting from compounds I in which R contains a basic function, and from mineral or organic acids and by recrystallisation of these salts in a suitable solvent. These salts are also included in the present invention.

The compounds of the general formula I and their physiologically tolerable salts have valuable pharmacological and therapeutic properties, especially cell membrane potential modulating properties.

These substances, which activate membrane potassium channels, increase an outward potassium flow and thus induce membrane hyperpolarisation.

The mechanism of action of this new pharmacological class renders possible an original approach to the anomalies of cell membrane potential regulation and cell ion regulation, including modulation of the transmembrane and intracellular calcium movements, in addition to modulation of potassium fluxes. These anomalies are involved in numerous physiopathological processes associated especially with disorders in the regulation of the contraction of the various types of smooth muscle.

Pharmacological tests carried out in vitro show that these products have a strong vascular relaxant activity compatible with an activation of membrane potassium channels.

Tested in vivo on arterial hypertension models in the rat and the dog, these substances, when administered orally, have a strong antihypertensive activity which lasts very much longer than that of all currently described compounds having such a mechanism of action, especially CROMAKALIM, which is the nearest product of the prior art.

Haemodynamic studies carried out on dogs demonstrate the strength and the long duration of their peripheral and coronary vasodilative effect.

These properties enable the compounds of the invention to be used as medicaments, especially in the cardiovascular field: systemic and pulmonary arterial hypertension, myocardial ischaemia, peripheral vascular diseases and cardiac insufficiency, and, more generally, the treatment and prevention of disorders connected with arterial ageing and atherosclerosis. They can also be used in metabolic pathologies constituting a cardiovascular risk factor, such as: obesity, diabetes and dyslipidemias.

In addition, the activity of these compounds on the various types of smooth muscle enables their therapeutic range to be extended to conditions associated with disorders in the regulation of smooth muscle contraction in the bronchopulmonary (obstructive bronchopneumopathy, asthma), digestive, urinary and uterine fields.

Those therapeutic indications are not limiting inasmuch as the deterioration of cell membrane potential, whatever the cause, and tissue localisation result in cell disfunction, the origin of pathological phenomena, and may constitute a major therapeutic target of the products described.

Thus, a number of conditions of tissue disorder, whether associated with ageing, ischaemia, inflammation or oedema (especially at the cerebral level), can be treated or prevented by the products of the present invention.

The present invention also relates to pharmaceutical compositions containing as active ingredient a compound of the general formula I or one of its physiologically tolerable salts, mixed or associated with a suitable pharmaceutical excipient, such as, for example, distilled water, starch, talc, ethylcellulose or magnesium stearate.

The pharmaceutical compositions so obtained are generally presented in dosage form and may contain from 0.05 to 50 mg of active ingredient. They may, for example, be in the form of tablets, dragees, soft gelatin capsules, suppositories, injectable or drinkable solutions as well as in the forms suitable for administration by aerosol and may, depending on the case, be administered orally, rectally or parenterally at a dose of from 0.05 to 50 mg, once or twice per day.

The following Examples illustrate the invention.

EXAMPLE 1:

3R,4S- or 3S,4R-trans-2,2-dimethyl-3-hydroxy-4-(2-oxo-5S-hydroxymethyl-1-pyrrolidinyl)-6-cyanochroman (A and B forms)

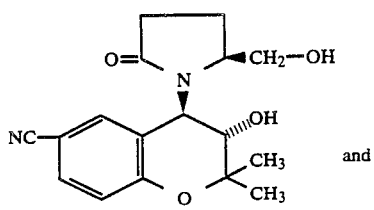

and

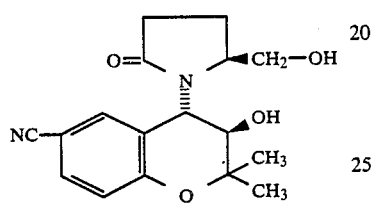

39 ml of a 1.6M butyllithium solution in hexane are added at 15°–20° C. to a solution of 10.5 g of S(1-ethoxy-5-ethoxymethyl)-2-pyrrolidone in 20 ml of hexamethylphosphorotriamide. The whole is shaken for 30 minutes at 20° C. and then 14.1 g of 6-cyano-2,2-dimethyl-3,4-epoxychroman which melts (capillary) at 97°–98° C. are added. The whole is heated for 20 hours at 35° C., cooled and 3.7 ml of acetic acid are added while shaking for 30 minutes at 5°–10° C. Dilution is effected with 200 ml of water and shaking is again carried out for 30 minutes at 5°–10° C. An oily product separates out. The aqueous liquor is decanted and the oil is taken up again with 150 ml of water. A precipitate is then formed. $CH_2Cl_2$ is added, the whole is shaken and the organic layer is decanted. After evaporation, 23 g of crude oil are obtained which are dissolved in 100 ml of methanol. The solution is shaken with 50 ml of 0.1N HCl for 2 hours to eliminate the protecting group. After evaporation of the solvent or flash column chromatography through 1 kg of silica using the system $CH_2Cl_2$/methanol 95:5 as eluant, two pure fractions, $R_f$=0.46 and 0.49, are isolated which correspond to the two pure diastereoisomers:

form A: 4.6 g m.p. (cap)=152°–153° C., $[\alpha]_D^{20\cdot 5} = -32.7°$ (c=1 EtOH).

form B: 3.8 g m.p. (cap)=156°–158° C., $[\alpha]_D^{20\cdot 5} = -62.9°$ (c=1 EtOH).

The S-(1-ethoxy-5-ethoxymethyl)-2-pyrrolidone used as starting material (oil) $[\alpha]_D^{20\cdot 5} = +21.8°$ (c=1 EtOH) was prepared, with a yield of 96%, by adding ethyl vinyl ether in $CHCl_3$, in the presence of $CF_3COOH$, to 5S-hydroxymethyl-2-pyrrolidone (oil) $[\alpha]_D^{21} = +33°5$ (c=3 EtOH).

EXAMPLE 2:

3S,4R- or 3R,4S-trans-2,2-dimethyl-3-hydroxy-4-(2-oxo-5S-methoxymethyl-1-pyrrolidinyl)-6-cyanochroman (A and B forms)

and

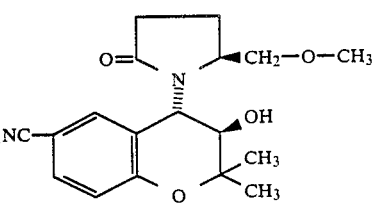

The forms:

A, $[\alpha]_D^{21} = -69.6°$ (c=1 EtOH), M.P. (cap)=186°–189° C. and

B, $[\alpha]_D^{21} = +1.22°$ (c=1 EtOH), M.P. (cap)=142°–145° C.

were prepared in accordance with the method described in Example 1, starting from 5S-methoxymethyl-2-pyrrolidone (oil), which was itself prepared starting from 5S-hydroxymethyl-2-pyrrolidone and dimethyl sulphate in the presence of sodium hydroxide, with a yield of 60%.

EXAMPLE 3:

3R,4S- or 3S,4R-trans-2,2-dimethyl-3-hydroxy-4-(2-oxo-5S-dimethylaminomethyl-1-pyrrolidinyl)-6-cyanochroman, (A and B forms):

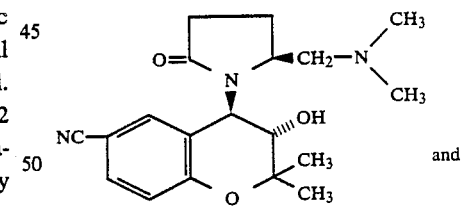

and

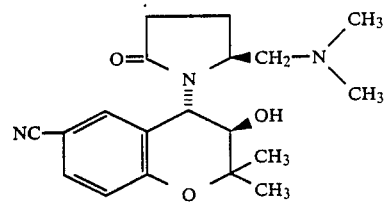

The forms:

A, m.p. (cap)=153°–156° C., $[\alpha]_D^{20\cdot 5} = -39°$ (c=1 DMSO)

B oxalate, m.p. (cap)=194°–197° C., $[\alpha]_D^{20\cdot 5} = -41.1°$ (c=1 EtOH).

were prepared in accordance with the method described in Example 1 starting from 5S-dimethylaminomethyl-2-pyrrolidone (oil) of 96% optical purity (HPLC), which was itself prepared by heating 5S-chloromethyl-2-pyrrolidone (oil) of 94% optical purity (HPLC, chiral column) at 100° C. with an excess of dimethylamine in ethanol.

EXAMPLES 4–30:

By proceeding as in Example 1, and using suitable starting materials, the products forming the subject of the following Examples (A and B forms) were prepared:

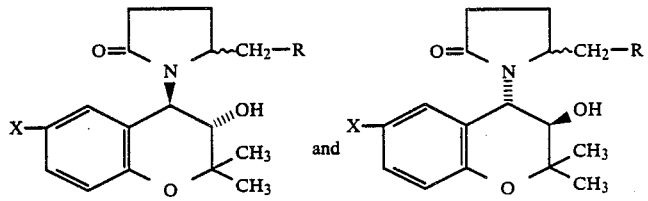

| n° Ex | X | R |
|---|---|---|
| 4 | —CN | —O—CO—CH$_3$ |
| 5 | —CN | —O—(CH$_2$)$_5$—CH$_3$ |
| 6 | —CN | —O—CH$_2$CH$_2$—O—CH$_3$ |
| 7 | —CN | —O—(CH$_2$)$_2$—N(—CH$_3$)$_2$ |
| 8 | —CN | —O(CH$_2$)$_2$—N(—C$_2$H$_5$)$_2$ |
| 9 | —CN | —N(—C$_2$H$_5$)$_2$ |
| 10 | —CN | —N(piperidinyl) |
| 11 | —CN | —N(morpholinyl) |
| 12 | —CN | —N(piperazinyl)N—CH$_3$ |
| 13 | —CN | —N(piperazinyl)N—CH(—C$_6$H$_5$)$_2$ |
| 14 | —CN | —N(piperazinyl)NCH$_2$-(3,4-methylenedioxyphenyl) |
| 15 | —CN | —N(piperazinyl)N—CH$_2$—CH=CH—C$_6$H$_5$ |
| 16 | —CN | —N(piperazinyl)N—C$_6$H$_5$ |
| 17 | —CN | —N(piperazinyl)N—(pyrimidin-2-yl) |
| 18 | —CN | —N(piperazinyl)N—(thiazol-2-yl) |

-continued

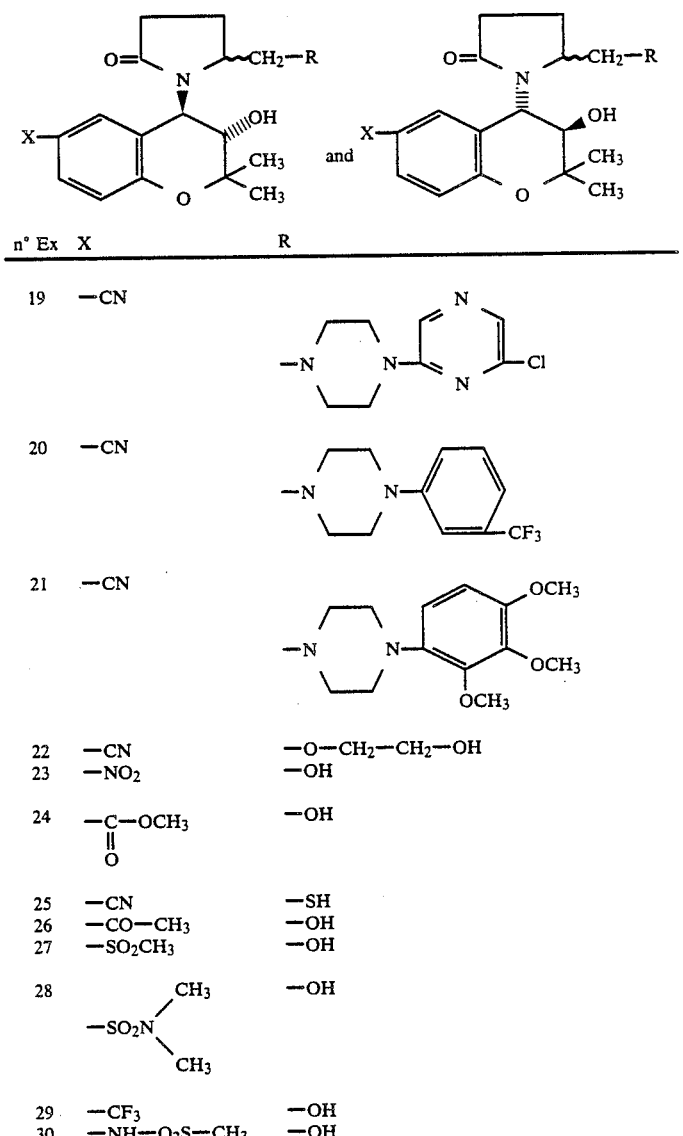

| n° Ex | X | R |
|---|---|---|
| 19 | —CN | -N(piperazine)N-CH=N-CH=CH-Cl (pyrazinyl-chloro) |
| 20 | —CN | -N(piperazine)N-C6H4-CF3 |
| 21 | —CN | -N(piperazine)N-C6H2(OCH3)3 |
| 22 | —CN | —O—CH2—CH2—OH |
| 23 | —NO2 | —OH |
| 24 | —C(=O)—OCH3 | —OH |
| 25 | —CN | —SH |
| 26 | —CO—CH3 | —OH |
| 27 | —SO2CH3 | —OH |
| 28 | —SO2N(CH3)2 | —OH |
| 29 | —CF3 | —OH |
| 30 | —NH—O2S—CH3 | —OH |

EXAMPLE 20:

Pharmacological study in vitro in the cardiovascular field:

Male Wistar rats (325–375 g) are anaesthetised i.p. using sodium pentobarbital (30 mg/kg). The thoracic aorta and the mesenteric portal vein are removed. The aorta is dissected into rings 3 mm long and the endothelium is removed mechanically.

1 cm of the portal vein is cut out and attached at its ends.

The organs are placed in a 20 ml thermostatically controlled vessel containing a physiological solution composed of (mM): NaCl 112; KCl 5; $KH_2PO_4$ 1; $MgSO_4$ 1.2; $CaCl_2$ 2.5; $NaHCO_3$ 25; glucose 11.5; EDTA 0.1; pH: 7.4; 37° C.; 95% $O_2$+5% $CO_2$.

The initial force applied is 2 g in the case of the aorta and 0.5 g in the case of the portal vein. The variations in force are measured by a STATHAM sensor connected to a transducer amplifier (GOULD) and are monitored continuously on a GOULD 2400 graphic recorder.

The experimental protocols are as follows: After a stabilisation period of 90 minutes, the aortic rings are subjected to various tests:

potassium depolarisation:

The preparations are exposed to a 30 mM or 80 mM KCl (and 87 and 37 mM NaCl, respectively) hyperpotassium medium; after 30 minutes' stabilisation of contraction, cumulative concentrations of the product to be tested are added every 15 minutes. The relaxation values obtained allow the $IC_{50}$s to be calculated.

reactivity to 4-aminopyridine (4 AP)

The product to be tested, at a given concentration, or its solvent, is incubated in the normal physiological solution 15 minutes before the addition of the 4 AP (5 mM).

The maximum amplitudes of the responses to the 4 AP in the presence of the product or the solvent are compared.

The portal vein exhibits a stable spontaneous rhythmic activity in 60 minutes. Cumulative concentrations of the product to be tested are added to the medium every 15 minutes; the frequency and amplitude variations of the peaks are recorded.

The products are used in a form dissolved in water or a suitable solvent.

The concentrations expressed refer to the final concentrations in terms of base in the isolated organ baths.

The results obtained are grouped in the following Table:

| Products tested | AORTA OF THE RAT | | | | PORTAL VEIN Suppression of rhythmic activity (M) |
|---|---|---|---|---|---|
| | $IC_{50}(M)$ 30 mM | KCl 80 mM | % inhibition of the response to 4AP according to the concentration of product (M) | | |
| CROMAKALIM | $4.2 \times 10^{-7}$ | $>10^{-4}$ | 13% 74% | $(10^{-7})$ $(10^{-5})$ | $3 \times 10^{-7}$ |
| Ex. 1 Form A | $7.7 \times 10^{-6}$ | $>10^{-4}$ | 35% | $(10^{-5})$ | $10^{-5}$ |
| Ex. 1 Form B | $3.4 \times 10^{-7}$ | $>10^{-4}$ | 18% 77% | $(3 \times 10^{-6})$ $(10^{-5})$ | $3 \times 10^{-7}$ $10^{-5}$ |
| Ex. 2 Form A | $2.8 \times 10^{-7}$ | $>10^{-4}$ | | | |

Examination of this Table shows that:

The products tested have a strong vascular relaxant activity in a medium depolarised by a low potassium concentration (30 mM), the activity disappearing at a high potassium concentration (80 mM).

The vascular contractions induced by 4-aminopyridine (antagonist of potassium channels) are strongly inhibited by these compounds.

The spontaneous rhythmic activity of the portal vein, which is sensitive to the variation in membrane potential, is greatly impaired by the products described.

These results, taken as a whole, are compatible with a membrane hyperpolarising mechanism of action by activation of potassium channels.

The strength of activity of the product of Example 1, form B, is comparable in these tests to that of the strongest reference product known: CROMAKALIM.

EXAMPLE 21:

Pharmacological study in vivo in the cardiovascular field

A- The study comprises the following tests:

1- STUDY ON THE SPONTANEOUSLY HYPERTENSIVE RAT (SHR)

1-1- METHODOLOGY

The study is carried out on SHR male rats (Charles River) weighing from 260 g to 330 g and aged from 18 to 20 weeks. A polyethylene catheter is positioned at the level of the abdominal aorta and tunnelised at the level of the neck under anaesthesia (ketamine hydrochloride 150 mg/kg intraperitoneally). The animals, placed in movement-restraining cages, are tested in the conscious state at least 48 hours after intervention. The arterial pressure, measured by a STATHAM P23 pressure sensor connected to the abdominal catheter, is registered on a GOULD 2400 recorder. The products are administered orally in dissolved form (water or suitable solvent) at a dose of 2.5 mg/kg. The doses administered are expressed in mg/kg of base.

1-2- RESULTS

The results obtained with a certain number of representative products of the invention and a reference product, CROMAKALIM, are grouped in the following Table. The variations in systolic and diastolic arterial pressure (PAS and PAD) presented at the most significant times after treatment are expressed as percentage variation with respect to the control values.

| Products tested | DOSE mg/kg | | CONTROL VALUES mmHg | VARIATIONS (%) AS A FUNCTION OF TIME AFTER TREATMENT | | | |
|---|---|---|---|---|---|---|---|
| | | | | 30 min | 1 H | 3 H | 6 H |
| CROMAKALIM | 0.3 | 6 | PAS 202 ± 9 | −29 ± 2 | −21 ± 3 | −5 ± 4 | −1 ± 2 |
| | | | PAD 129 ± 6 | −34 ± 2 | −26 ± 3 | −7 ± 5 | −3 ± 1 |
| CROMAKALIM | 1.0 | 6 | PAS 211 ± 10 | −34 ± 5 | −23 ± 4 | −19 ± 3 | −15 ± 2 |
| | | | PAD 136 ± 8 | −44 ± 4 | −33 ± 3 | −25 ± 4 | −20 ± 2 |
| Example 1 form B | 0.3 | 4 | PAS 219 ± 7 | −27 ± 5 | −27 ± 4 | −25 ± 3 | −29 ± 3 |
| | | | PAD 146 ± 5 | −34 ± 6 | −36 ± 4 | −35 ± 4 | −40 ± 4 |
| Example 1 form B | 1.0 | 4 | PAS 213 ± 5 | −42 ± 2 | −44 ± 1 | −40 ± 2 | −36 ± 3 |
| | | | PAD 135 ± 5 | −48 ± 5 | −54 ± 2 | −46 ± 6 | −46 ± 4 |
| Example 2 form A | 1.0 | 5 | PAS 192 ± 4 | −11 ± 2 | −16 ± 3 | −12 ± 3 | −9 ± 2 |
| | | | PAD 118 ± 3 | −17 ± 3 | −21 ± 4 | −19 ± 3 | −14 ± 2 |
| Example 2 form A | 3.0 | 6 | PAS 203 ± 3 | −24 ± 1 | −26 ± 2 | −25 ± 3 | −21 ± 3 |
| | | | PAD 130 ± 3 | −35 ± 3 | −36 ± 3 | −31 ± 3 | −27 ± 3 |

1-3- CONCLUSION OF THE IN VIVO STUDY ON SHR

The products of the invention have a remarkable antihypertensive activity in SHR rats after oral administration of low doses. The duration of action of the products described is considerably prolonged compared with that of the best reference product known, CROMAKALIM, with a comparable maximum activity, and constitutes an important therapeutic advantage.

2- STUDY ON THE CONSCIOUS RENALLY HYPERTENSIVE DOG 2-1- METHODOLOGY

Mongrel dogs weighing from 20 to 25 kg are used. A silastic catheter positioned under anaesthesia (sodium pentobarbital 30 mg/kg i.v.) at the level of the abdominal aorta and left over a prolonged period permits the later measurement of the arterial pressure in the conscious animals. Arterial hypertension is induced by a second intervention under anaesthesia consisting in a constriction of the left renal artery using a clip, which reduces its rate of flow by approximately 70%, the left kidney is enveloped in a latex capsule and the contralateral kidney is left in place.

The systolic and diastolic arterial pressures (PAS and PAD) are measured using a STATHAM P23 pressure sensor connected to the silastic catheter and linked to a GOULD pressure amplifier. The products are tested on the animals, which have become hypertensive, in the conscious state, at least one week after the second intervention. The arterial pressure is monitored continuously on an ES1000 GOULD recorder until 7 hours have elapsed after the treatment and then until 24 hours have elapsed.

The products to be tested are administered via the digestive system, after gastric intubation, in a form dissolved in water or a suitable solvent. The doses administered are expressed in mg of base with respect to body weight.

2-2- RESULTS

The representative products of the invention were compared with the reference product (CROMAKA- GOULD SP 2202 electromagnetic flow meters. The aortic pressure is measured by a MILLAR probe introduced via the femoral artery.

The total peripheral vascular resistance values (TPR) and the mean coronary vascular resistance values (CVRM) are calculated by the ratio between the mean aortic pressure and the mean cardiac output and the mean coronary output, respectively. The products tested were injected via the femoral vein in a form dissolved in water or a suitable solvent.

3-2- RESULTS

The results obtained with the tested products of the invention are compared with the reference product CROMAKALIM.

The evolution of the vascular resistances, expressed as percentage variation with respect to the control values, is presented as a function of time in the following Table.

| Products tested | DOSE µg/kg | PARAMETER | VARIATION (%) AS A FUNCTION OF TIME AFTER TREATMENT | | |
|---|---|---|---|---|---|
| | | | 1 min | 10 min | 30 min |
| CROMAKALIM | 10 | CVRM | −69.0 | −38.1 | −27.4 |
| | | TPR | −26.8 | −15.5 | −7.8 |
| Example 1 form B | 10 | CVRM | −69.4 | −62.0 | −43.7 |
| | | TPR | −45.9 | −35.1 | −35.1 |
| Example 1 form A | 300 | CVRM | −81.5 | −50.3 | −34.9 |
| | | TPR | −41.9 | −17.2 | −12.9 |
| Example 2 form A | 30 | CVRM | −28.9 | −20.2 | −22.1 |
| | | TPR | −9.8 | −11.8 | −11.8 |
| Example 2 form A | 100 | CVRM | −54.7 | −56.1 | −50.5 |
| | | TPR | −15.8 | −14.7 | −12.6 |
| Example 3 form A | 3000 | CVRM | +2.5 | −38.5 | −49.0 |
| | | TPR | +1.7 | −6.8 | −8.5 |

LIM). The variations in the systolic and diastolic arterial pressures (PAS and PAD), presented at the most significant times after treatment, are expressed as percentage variation with respect to the control values.

| Products tested | DOSE mg/kg | CONTROL VALUES mmHg | VARIATIONS (%) AS A FUNCTION OF TIME AFTER TREATMENT | | | | |
|---|---|---|---|---|---|---|---|
| | | | 30 min | 1 H | 3 H | 7 H | 24 H |
| CROMAKALIM | 0.1 | PAS 189 | −50 | −26 | −9 | +2 | +9 |
| | | PAD 93 | −46 | −23 | −9 | −5 | +18 |
| Example 1 form B | 0.1 | PAS 199 | 0 | +2 | −55 | −76 | −24 |
| | | PAD 99 | 0 | +5 | −50 | −68 | −27 |
| Example 2 form A | 0.1 | PAS 181 | −2 | −12 | −28 | −41 | −2 |
| | | PAD 93 | −14 | −20 | −32 | −44 | 0 |

2-3- CONCLUSION OF THE IN VIVO STUDY IN THE RENALLY HYPERTENSIVE DOG

Strong antihypertensive activity and long duration of action of these products is observed in the renally hypertensive dog. The superiority of the product of Example 1, form B, in terms of strength and duration of action in comparison with CROMAKALIM is to be especially underlined.

3- HAEMODYNAMIC STUDY IN THE ANAESTHETISED DOG 3-1- METHODOLOGY

A complete haemodynamic study was carried out on mongrel dogs weighing from 25 to 30 kg, which were anaesthetised with sodium pentobarbital 30 mg/kg i.v., intubated and ventilated and subjected to a thoracotomy at the 5th left intercostal space. The measurement of the mean coronary and cardiac outputs is carried out using electromagnetic rings positioned at the level of the ascending aorta and the circumflex branch of the left coronary artery, respectively, and connected to 3-3- CONCLUSION OF THE HAEMODYNAMIC STUDY ON THE DOG Administered intravenously at a low dose, the compounds of the invention have a strong peripheral and coronary vasodilative activity which is better maintained than that of CROMAKALIM.

B- In general, all of the in vivo tests carried out permit the conclusion that the compounds of the present invention have an activity which is comparable or superior to that of the best reference product known (CROMAKALIM) while at the same time having a duration of action very much greater than that of the latter, which constitutes a major advantage for therapeutic use.

EXAMPLE 22:

Pharmacological study in the bronchopulmonary field:

The bronchodilating activity has been studied in the guinea pig by the method of H. KONZETT and R. ROSSLER, Arch. Exp. Path. U. Pharm. 195, 71 (1940).

It has been observed that the compounds of the present invention injected intravenously at doses varying, according according to the compounds, from 0.3 to 1 mg/kg inhibit notably the bronchospasm provoked by the intravenous administration either of histamine or serotonin or acetylcholine.

For example, the bronchospasm produced in the guinea pig by a histamine aerosol et 4% is inhibited of 96% by the compound of Example 1 B form, at the dose of 0.30 mg/kg i.v., and of 100% by the compound of Example 24 B form, at the dose of 0.35 mg/kg i.v.

When submitted to the test of A. K. ARMITAGE, Brit. J. Pharmacol. 17, 196 (1961), the tested compounds, administered by oral route or aerosol at doses between 0.5 to 4 mg/kg, depending on the compounds, inhibit of from 11 to 68% the effect produced in the guinea pig by a histamine aerosol at 4%.

EXAMPLE 23:

Pharmaceutical preparation:

Soft gelatin capsules containing 1 mg of active ingredient

| | |
|---|---|
| 3R, 4S- or 3S, 4R-trans-2,2-dimethyl-3-hydroxy-4-(2-oxo-5S-hydroxymethyl-1-pyrrolidinyl)-6-cyanochroman | 1 mg |
| corn starch | 15 mg |
| lactose | 25 mg |
| talc | 5 mg |

We claim:

1. A compound selected from the group consisting of: amino chromanol compounds of formula I:

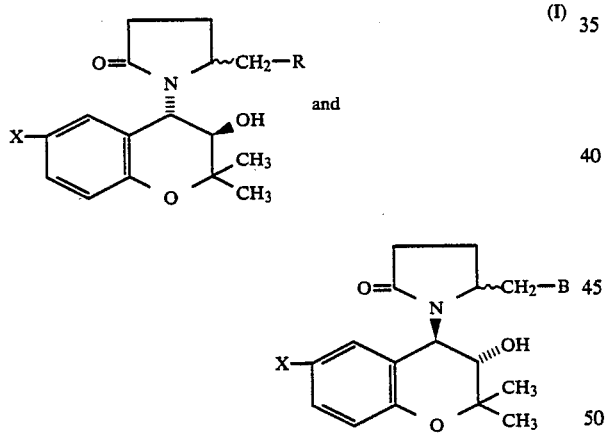

in which:
X is selected from the group consisting of: cyano, nitro, trifluoromethyl, alkoxycarbonyl in which the alkoxy group contains 1 to 5 carbon atoms, carbamido, dialkylcarbamido, aminosulfonyl, dialkylaminosulfonyl, alkylsulfonyl and alkylsulfonylamino in which the alkyl groups each contain 1 to 5 carbon atoms, and acyl selected from: acetyl, propionyl, benzoyl and trifluoroacetyl;
CH$_2$-R is attached (in the 5 position of the pyrrolidinone nucleus) to an R- or S- configured carbon atom, and R is selected from the group consisting of:

(a) —OR' and —SR' radicals in which R' is selected from the group consisting of:
hydrogen;
alkyl and hydroxyalkyl having up to 10 carbon atoms, and such radical interrupted by an oxygen atom;
alkylcarbonyl in which alkyl contains up to 5 carbon atoms;

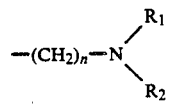

in which:
n is an integer from 2 to 5, and R$_1$ and R$_2$, which are identical or different, are each selected from the group consisting of:
hydrogen,
alkyl having 1 to 5 carbon atoms, and (b)

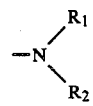

in which R$_1$ and R$_2$ have the meanings given above, and
physiologically-tolerable acid addition salts of the compounds of the formula I wherein R contains a basic function.

2. A compound of claim 1 which is:
3R, 4S or 3S, 4R-trans-2,2-dimethyl-3-hydroxy-4-(2-oxo-5S-hydroxymethyl-1-pyrrolidinyl)-6-cyanochroman, A or B form.

3. A compound of claim 1 which is:
3S, 4R or 3R, 4S-trans-2,2-dimethyl-3-hydroxy-4-(2-oxo-5S-methoxymethyl-1-pyrrolidinyl)-6-cyanochroman, A or B form.

4. A compound of claim 1 which is:
3R, 4S or 3S, 4R-trans-2,2-dimethyl-3-hydroxy-4-(2-oxo-5S-dimethylaminomethyl-1-pyrrolidinyl)-6-cyanochroman, A or B form.

5. A compound of claim 1 which is:
3R, 4S or 3S, 4R-trans-2,2-dimethyl-3-hydroxy-4-(2-oxo-5S-hydroxymethyl-1-pyrrolidinyl)-6-nitrochroman, A or B form.

6. A compound of claim 1 which is:
3R, 4S or 3S, 4R-trans-2,2-dimethyl-3-hydroxy-4-(2-oxo-5S-hydroxymethyl-1-pyrrolidinyl)-6- methoxycarbonylchroman, A or B form.

7. Pharmaceutical composition useful in the treatment of disorders requiring the activation of potassium channels and connected with regulation of smooth muscle and vascular tissue contraction, containing as active ingredient an amount of a compound of claim 1 which is effective for such purpose together with a pharmaceutically-acceptable carrier.

8. A method for treating a living animal afflicted with a disorder requiring the activation of potassium channels and connected with regulation of smooth muscle and vascular tissue contraction, cardiovascular, bronchopulmonary, digestive, urinary an uterine fields, ischaemic, inflammatory, oedematous or proliferative pathologies at the organ or cutaneous level, or metabolic diseases involving obesity and a disorder of glycoregulation, comprising the step of administering to the said living animal an amount of a compound of claim 1 which is effective for such purpose and for the alleviation of the said disorder.

* * * * *

UNITED STATES PATENT AND TRADEMARK OFFICE
CERTIFICATE OF CORRECTION

PATENT NO. : 4,999,372

DATED : Mar. 12, 1991

INVENTOR(S) : Gilbert Regnier, Alain Dhainaut, Jean-Paul Vilaine, Nicole Villeneuve, Ghislaine Joly, Jacques Duhault It is certified that error appears in the above-identified patent and that said Letters Patent is hereby corrected as shown below:

Column 13/14, second table, beginning approximately line 31, third column of the table; insert the heading -- N --.
Column 17, line 1; delete "according, second occurrence.
Column 17, line 6; "et" should read -- at --.
Column 18, line 60; "an" should read -- and --.

Signed and Sealed this

Eighth Day of December, 1992

Attest:

DOUGLAS B. COMER

Attesting Officer

Acting Commissioner of Patents and Trademarks